United States Patent
Ouchi

(10) Patent No.: US 6,790,176 B2
(45) Date of Patent: Sep. 14, 2004

(54) PROBE OF ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/902,004

(22) Filed: Jul. 10, 2001

(65) Prior Publication Data

US 2002/0026100 A1 Feb. 28, 2002

(30) Foreign Application Priority Data

Jul. 11, 2000 (JP) .................................... P2000-209898

(51) Int. Cl.$^7$ .............................. A61B 1/07; G02B 6/06
(52) U.S. Cl. ..................................... 600/182; 385/117
(58) Field of Search .................. 600/182; 385/116, 385/117

(56) References Cited

U.S. PATENT DOCUMENTS 4,566,438 A * 1/1986 Liese et al. .................. 600/129
4,834,518 A * 5/1989 Barber ....................... 359/375

FOREIGN PATENT DOCUMENTS

JP 6-194582 * 7/1994 ........... G02B/23/26

* cited by examiner

*Primary Examiner*—John P. Leubecker
(74) *Attorney, Agent, or Firm*—Pitney Hardin LLP

(57) ABSTRACT

A probe of an endoscope comprises a light guide fiber bundle and an image guide fiber bundle. The light guide fiber bundle supplies illumination light to the distal end of the probe, to illuminate the observed object. The illumination light is reflected by the observed object, and enters the end surface of the image guide fiber bundle. A ratio of an illumination sectional area of the light guide fiber bundle to a light receiving sectional area of the image guide fiber bundle is made equal.

6 Claims, 4 Drawing Sheets

PROBE OF ENDOSCOPE

BACKGROUND OF THE INVENTION

1. Field of the Invention

The present invention relates to a probe of an endoscope, which has an image receiving optical element, including an image guide fiber bundle and an imaging device, and an illumination optical system provided with a light guide fiber bundle.

2. Description of the Related Art

Usually, a medical endoscope for observing the inside of a human body, and an industrial endoscope for observing the inside of a machine, are provided with an illumination optical system and an image receiving optical element. Namely, the inside of the body or the machine is illuminated by the illumination optical system, and an image of the observed object illuminated by the illumination optical system is received and transmitted to an operation unit of the endoscope by the image receiving optical element. The endoscopes have a probe, which is inserted into the body or the machine and includes a flexible tube, a bendable tube, and a distal end. The inside of the probe is essentially provided with a light guide fiber bundle, which is a part of the illumination optical system, and an image receiving optical element. The image receiving optical element of a fiber-optic endoscope is an image guide fiber bundle,which senses an observed object image formed by an objective optical system and transmits the image as optical information. The image receiving optical element of an electronic endoscope is an imaging device, which senses the observed object image and transforms the image to an electric signal.

In the light guide fiber bundle, as the illumination sectional area (i.e., the sum of the sectional area of cores of optical fibers forming the light guide fiber bundle) becomes large, the illumination amount of light which can be transmitted becomes great, and thus the observed object can be illuminated with bright light. Conversely, in the image receiving optical element, as the light receiving sectional area (i.e., the sum of the sectional area of cores of optical fibers forming the image guide fiber bundle, or the sum of areas of the light receiving cells, except the transfer gates, on the light receiving surface of the imaging device) becomes large, the amount of light which can be received becomes great, and thus a bright image can be transmitted. Namely, if the illumination sectional area of the light guide fiber bundle is made as large as possible while the light receiving sectional area of the image receiving optical element is made as large as possible, the observed object can be observed as a bright object.

On the other hand, the outer diameter and the inner diameter of the probe of the endoscope are limited, because the probe is inserted into a narrow internal space of a body, a machine etc., and because the inner wall is provided with a synthetic resin tube etc. so as to protect the light guide fiber bundle, and the image receiving optical element. Further, other than the light guide fiber bundle and the image receiving optical element, various contents including wires for bending the bendable tube, a biopsy forceps channel, and air and liquid supply tubes, in the case of a medical endoscope, for example, are housed in the probe, in which the inner diameter is limited. Therefore, the sectional area of the space, in which the light guide fiber bundle and the image receiving optical element can occupy, i.e., the accommodation space, is further limited.

Accordingly, when accommodating the light guide fiber bundle and the image receiving optical element in the probe, in which the sectional area of the accommodation space is limited as described above, a ratio of the illumination sectional area of the light guide fiber bundle to the light receiving area of the image receiving optical element should be optimized so as to maximize the brightness of the observed object image.

SUMMARY OF THE INVENTION

Therefore, an object of the present invention is to provide a probe of an endoscope, in which the ratio of the illumination sectional area of the light guide fiber bundle to the light receiving area of the image receiving optical element is optimized.

According to the present invention, there is provided a probe of an endoscope, comprising a distal end, in which an objective lens is disposed, a light guide fiber bundle and an image receiving optical element. The light guide fiber bundle supplies illumination light to the distal end. The image receiving optical element transmits an image of the observed object obtained by the objective lens. A ratio of an illumination sectional area of the light guide fiber bundle to a light receiving area of the image receiving optical element is in a range of 39:61 and 61:39.

When the range of the sectional areas is between 39:61 and 61:39, and the sum of the sectional areas of the light guide fiber bundle and the sum of the areas of the image receiving optical element is fixed, the amount of light of the observed object image transmitted by the image receiving optical element is between the maximum and 95% of the maximum. Therefore, even though the sectional area of the accommodation space of the probe is limited, a bright object can be effectively obtained.

Note that, even within the range of the ratio described above, if the illumination sectional area of the light guide fiber bundle and the light receiving area of the image receiving optical element are made equal to each other, the observed object image becomes brightest.

The image receiving optical element is an image guide fiber bundle when the endoscope is a medical endoscope, and is an imaging device when the endoscope is an electronic endoscope. When the image receiving optical element is an image guide fiber bundle formed by bundling optical fibers, the light receiving area is a light receiving sectional area corresponding to the sum of sectional areas of cores of the optical fibers. When the image receiving optical element is an imaging device having light receiving cells, the light receiving area is an effective light receiving area corresponding to the sum of areas of the light receiving cells.

Further, according to the present invention, there is provided a probe of an endoscope, comprising a light guide fiber bundle and an image receiving optical element. The light guide fiber bundle supplies illumination light to the distal end of the probe, so that the illumination light is radiated onto and reflected by the observed object. The image receiving optical element receives the reflected light. A ratio of an illumination sectional area of the light guide fiber bundle to a light receiving area of the image receiving optical element is in a range of 39 to 61 and 61 to 39.

BRIEF DESCRIPTION OF THE DRAWINGS

The objects and advantages of the present invention will be better understood from the following description, with reference to the accompanying drawings, in which.

DESCRIPTION OF THE PREFERRED EMBODIMENTS

Figure 1:
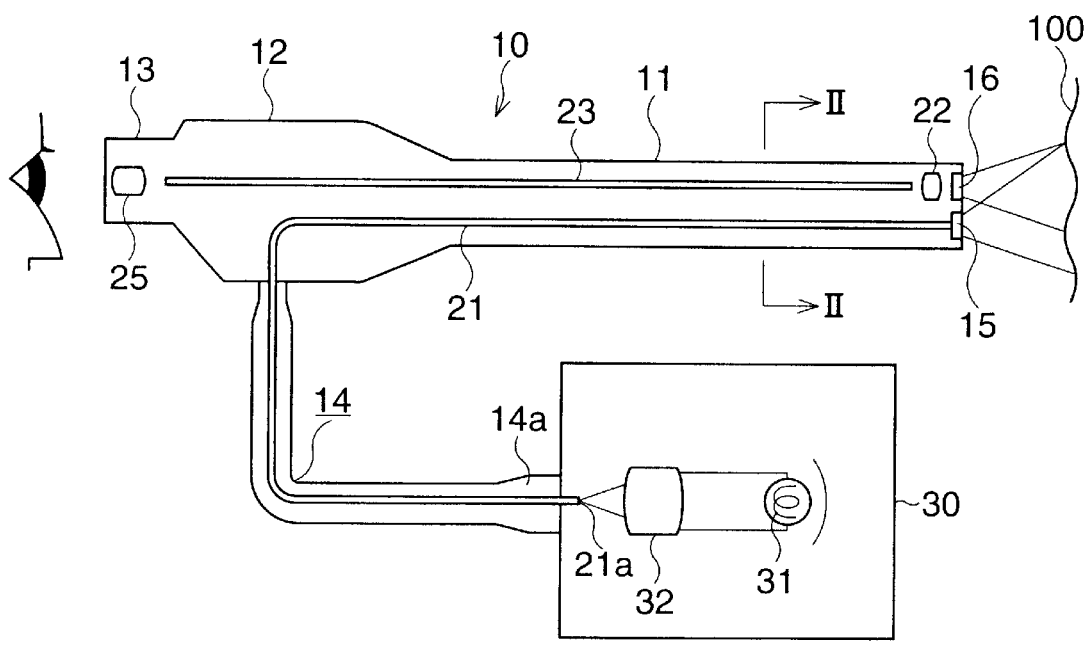
FIG. 1 is a schematic view of an endoscope system including a fiber-optic endoscope to which a first embodiment of the present invention is applied.

The present invention will be described below with reference to the embodiments shown in the drawings.

FIG. 1 is a schematic view showing an endoscope system including a fiber-optic endoscope 10 to which a first embodiment of the present invention is applied. As shown in FIG. 1, the endoscope system has the fiber-optic endoscope 10 and a light source device 30. The fiber-optic endoscope 10 is provided with a probe 11, which is inserted into the inside of a body or a machine, an operation unit 12 connected to an end portion of the probe 11, an eyepiece unit 13 fixed to an end portion of the operation unit 12, and a flexible light guide tube 14 projecting from a side surface of the operation unit 12.

The probe 11 is divided into a distal end located at an end thereof, a bendable tube, to which the distal end is fixed, and a flexible tube, which is located opposite to the distal end with respect to the bendable tube. At least two holes are formed in the distal end and are parallel to the longitudinal axis of the distal end. An observing window, which is a plane-parallel transparent plate 16, is fitted in the opening of the tip end of one of the holes, and a diffuser lens 15, which is a plano-concave lens, is fitted in the opening of the tip end of the other hole, in such a manner that the flat surface of the plano-concave lens faces the outside. The inside of the hole, in which the observing window 16 is fit, is provided with an objective lens 22 forming an image of an observed object 100. The bendable tube has a structure in which metal mesh and a synthetic resin tube are laminated on an outer surface of a segment formed by coaxially connecting a plurality of metal rings, and is freely bent in a predetermined direction by drawing operation wires, fixed to the end of the bendable tube, from the rear side. The flexible tube has a structure in which metal mesh and a synthetic resin tube are laminated on an outer surface of a spiral tube formed by winding a strip of metal in a spiral, and is arbitrarily bent in accordance with the external force.

An image guide fiber bundle (i.e., an image receiving optical element) 23 and a light guide fiber bundle 21 are inserted in the bendable tube and the flexible tube. An end portion of the image guide fiber bundle 23 is fixed to the hole, in which the objective lens 22 is provided in the end portion of the hole. The light guide fiber bundle 21 is provided in the hole, in which the diffuser lens 15 is fit in the end portion of the hole. In the bendable tube and the flexible tube, the operation wires, for bending the bendable tube, and contents, corresponding to the functions of the fiber-optic endoscope 10, are inserted. For example, in a medical endoscope, air and liquid supply tubes for cleansing an outer surface of the observing window 16, a biopsy forceps channel for leading the biopsy forceps to the end surface of the distal end, and so on, are inserted. Namely, in the internal space of the bendable tube and the flexible tube of the probe 11, a portion, other than a space which is provided for inserting the contents such as the operation wires, is an accommodation space where the image guide fiber bundle 23 and the light guide fiber bundle 21 can be provided.

Figure 2:
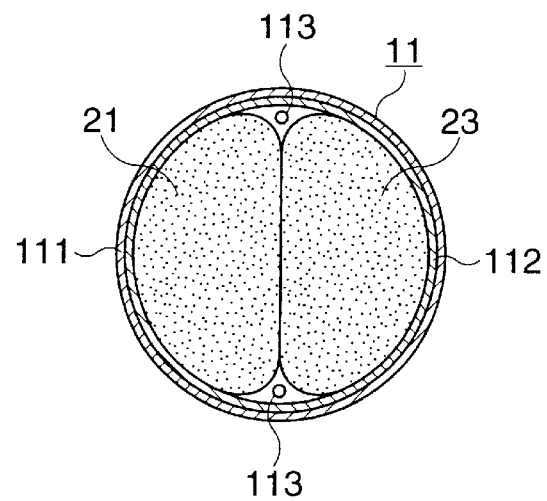
FIG. 2 is a vertical sectional view along the II—II line in FIG. 1.

FIG. 2 is a sectional view, along the II—II line in FIG. 1, of probe 11, showing a state in which the image guide fiber bundle 23 and the light guide fiber bundle 21 are fully packed in the accommodation space, wherein the fiber-optic endoscope 10 is an industrial endoscope or a nasopharyngoscope. In FIG. 2, the synthetic resin tube 111 is fitted on an outer surface of the segment (in the case of the bendable tube) or spiral tube (in the case of the flexible tube) 112, and the light guide fiber bundle 21 and the image guide fiber bundle 23 are accommodated in the segment or spiral tube 112. The operation wires 113 are housed in spaces formed between the light guide fiber bundle 21 and the image guide fiber bundle 23. Namely, the accommodation space is the portion other than the spaces in which the operation wires 113 are housed.

Both the light guide fiber bundle 21 and the image guide fiber bundle 23 are formed by bundling a plurality of optical fibers and both ends of the bundle are bound and fixed. The other portion between both ends is covered with a silicone tube.

The operation unit 12 (FIG. 1) is provided with a pulley (not shown), to which an end portion of each of the operation wires 113 is connected, and an operation dial, which is provided outside the operation unit 12 and is coaxially connected to the pulley. The operation dial is handled by the operator to rotate the pulley so that the operation wires 113 are tensioned to bend the bendable tube in an arbitral direction.

The image guide fiber bundle 23 passes through the operation unit 12 to reach the eyepiece unit 13. In the eyepiece unit 13, an eyepiece 25 is housed through which the operator can observe an enlarged image of the observed object 100, which is transmitted to the rear end surface of the image guide fiber bundle 23. Note that, by adjusting the position of the eyepiece 25, a real image of the image transmitted onto the rear end surface of the image guide fiber bundle 23 can be formed on a predetermined plane, and the real image can be taken by a silver-halide-film still camera or a video camera.

The light guide fiber bundle 21 is inserted from the operation unit 12 into the flexible light guide tube 14, and projects from the end of the flexible light guide tube 14, to which a connector 14a is attached and detachably connected to a receptacle provided on the light source device 30. In a state in which the connector 14a is connected to the receptacle of the light source device 30, an incident end surface 21a of the light guide fiber bundle 21 projects into the light source device 30.

In the light source device 30, a light source lamp 31 for radiating illumination light, and a condenser lens 32 for condensing the illumination light radiated from the lamp 31 onto the incident end surface 21a of the light guide fiber bundle 21, are housed.

In the endoscope system described above, most of the illumination light radiated from the light source lamp 31 of the light source device 30, is condensed by the condenser lens 32, and led to the incident end surface 21a of the light guide fiber bundle 21. The illumination light entering the light guide fiber bundle 21 is led in the probe 11 through the light guide fiber bundle 21 to the distal end, and radiated from the end face thereof. The radiated illumination light is diffused by the diffuser lens 15 to illuminate the observed object 100.

A part of the illumination light, diffusedly reflected by a surface of the observed object 100, passes through the observing window 16, and is converged by the objective lens 22, so that an image of the observed object 100 is formed on the front end surface of the image guide fiber bundle 23. The image is transmitted to the rear end surface through the image guide fiber bundle 23, being divided into pixels corresponding to the optical fibers. The image of the observed object 100 transmitted to the rear end surface of the image guide fiber bundle 23 is enlarged by the eyepiece 25 and observed by the operator.

The optimum ratio of an illumination sectional area of the light guide fiber bundle 21 to a light receiving sectional area of the image guide fiber bundle 23, in the accommodation space of the probe 11, is described below. For simplicity of the explanation, it is supposed that the light guide fiber bundle 21 and the image guide fiber bundle 23 have identical constructions, and light, which is made incident on the whole of the end surface of both the light guide fiber bundle 21 and the image guide fiber bundle 23, can be transmitted. Namely, a geometrically occupied sectional area of each of the fiber bundles 21 and 23 is equal to the illumination sectional area or the light receiving sectional area. Further, it is supposed that, in the light source device 30, a luminous flux of the illumination light entering the incident end surface 21a, the distance from the observing window 16 to the observed object 100, and the reflectance of the surface of the observed object 100 are always constant.

The sectional area of the accommodation space is normalized to "1". If the geometrically occupied sectional area of the light guide fiber bundle 21 is defined as "1/n", the maximum geometrically occupied sectional area of the image guide fiber bundle 23, which can be accommodated in the remaining space of the accommodation space, is "1−1/n". Under the assumption described above, the brightness x of the observed object illuminated by the light guide fiber bundle 21 having the geometrically occupied sectional area "1/n" is $$x = (1/n) \times L \tag{1}$$

wherein "L" is a constant representing the brightness of the observed object 100 illuminated by the illumination light passing through the light guide fiber bundle 21 having the unit illumination sectional area.

Regarding object light from the observed object 100 having the brightness X, or diffusedly reflected light from the surface of the observed object 100, the amount y of light transmitted through the image guide fiber bundle 23 is $$y = x \times (1 - 1/n) \times M \tag{2}$$

$$= (1/n) \times L \times (1 - 1/n) \times M$$

wherein "M" is a constant representing the amount of light entering the image guide fiber bundle 23 having the unit light receiving sectional area, the light being included in the object light from the observed object 100. Here, if L×M=1, formula (2) is transformed to formula (3).

$$y = 1/n - 1/n^2 \tag{3}$$

Figure 3:
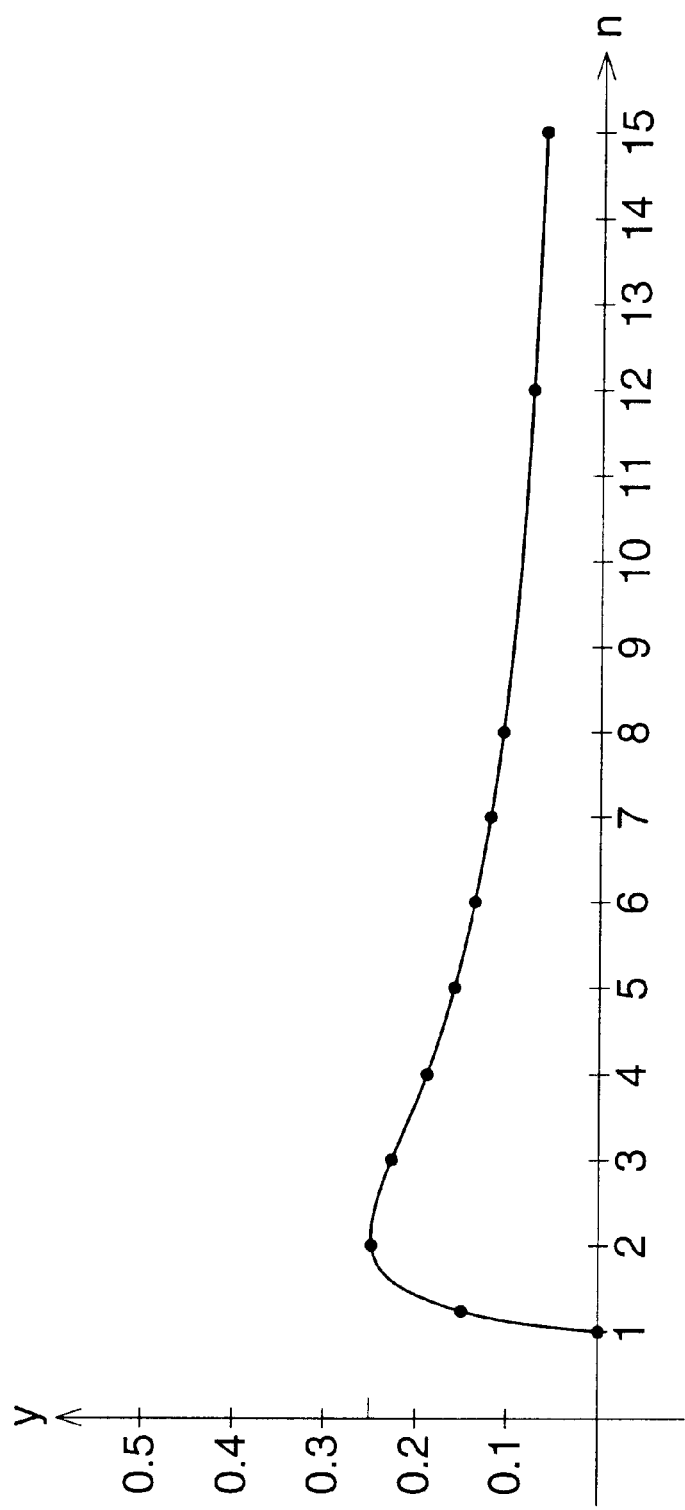
FIG. 3 is a graph showing a relationship between a variable "n" corresponding to the illumination sectional area and brightness of an observed object image.

From formula (3) represented graphically, as shown in FIG. 3, it is understood that "y" becomes the maximum value "0.25" when n=2. Namely, when the geometrically occupied sectional area (i.e., the illumination sectional area) of the light guide fiber bundle 21 is ½ of the sectional area of the accommodation space, and the geometrically occupied sectional area (i.e., the light receiving sectional area) of the image guide fiber bundle 23 is ½ of the sectional area of the accommodation space, the brightest image can be obtained. In other words, by equalizing the geometrically occupied sectional area (i.e., the illumination sectional area) of the light guide fiber bundle 21 to the geometrically occupied sectional area (i.e., the light receiving sectional area) of the image guide fiber bundle 23, the brightest image can be most efficiently obtained.

Figure 4:
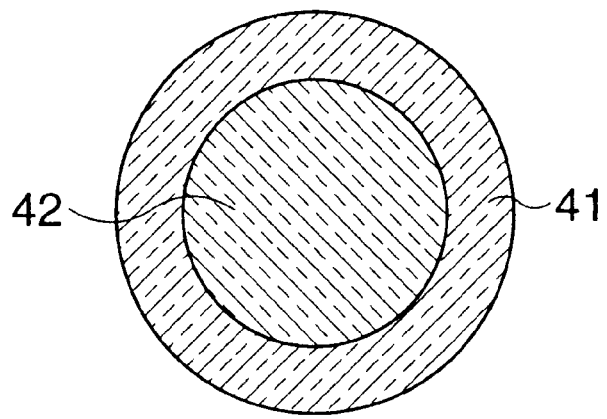
FIG. 4 is a sectional view of an optical fiber forming an image guide fiber bundle.
Figure 5:
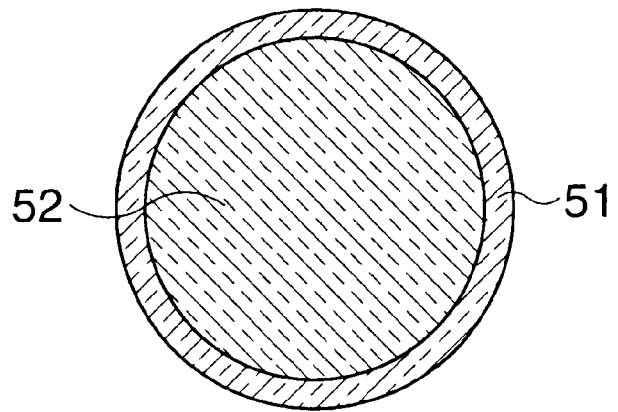
FIG. 5 is a sectional view of an optical fiber forming a light guide fiber bundle.

Note that, in reality, in the end surfaces of the fiber bundles 23 and 21, a part occupied by the silicone tube, a part occupied by gaps existing among the optical fibers, and a part occupied by cladding layers 41 (FIG. 4) and 51 (FIG. 5) of the optical fibers, cannot transmit light. Namely, in the geometrically occupied sectional area of each of the fiber bundles 23 and 21, the sum of only the sectional areas of cores 42 (FIG. 4) and 52 (FIG. 5) of the optical fibers is the actual illumination sectional area or light receiving sectional area.

Therefore, the conditions described above can be rewritten as follows: that is, regardless of the amount of the geometrically occupied sectional area of each of the fiber bundles 21 and 23, "If the illumination sectional area of the light guide fiber bundle 21 (i.e., the sum of sectional areas of cores of the optical fibers) and the light receiving sectional area of the image guide fiber bundle 23 (i.e., the sum of sectional areas of cores of the optical fibers) are made equal to each other, the brightest image can be most efficiently obtained (the optimum condition 1)".

Even if an exposure condition is determined based on the maximum brightness of the image of the observed object 100 transmitted to the rear end surface of the image guide fiber bundle 23, a silver-halide-film still camera or a video camera for taking an image of the observed object 100 through the eyepiece 25, can carry out a normal photography to obtain the brightest image, if the amount of light is decreased by 5% or so from the maximum, due to the latitude of the recording medium. On the other hand, if the difference of the amount of light is 5% or so, the naked eye of the operator, observing the image of the observed object 100 through the eyepiece 25, can normally observe the brightest image without being conscience of the difference in the amount of light. Accordingly, the conditions described above can be relaxed so as to include a range in which the amount of light is reduced by 5% or so from the maximum brightness of the image of the observed object 100.

Namely, by substituting y=0.25×0.95=0.2375 into formula (3), value of n=2.576 or n=1.6345 is produced. Accordingly, a range of the illumination sectional area $S_1$ of the light guide fiber bundle 21 is obtained as shown in formula (4).

$$1/2.576 < S_1 < 1/1.6345$$

$$0.39 < S_1 < 0.61 \tag{4}$$

Accordingly, a range of the light receiving sectional area $S_2$ of the image guide fiber bundle 23 corresponding to formula (4) is expressed as formula (5).

$$0.61 > S_2 > 0.39 \tag{5}$$

That is, "If, in the accommodation space of the probe 11, a ratio of the illumination sectional area $S_1$ of the light guide fiber bundle 21 to the light receiving sectional area $S_2$ of the image guide fiber bundle 23 is set as shown in formula (6), $$39:61 < S_1 : S_2 < 61:39 \tag{6}$$

an image of the observed object 100 can be obtained with sufficient brightness which is more than or equal to 95% of the maximum brightness (the optimum condition 2)".

On the other hand, especially in the case of the medical endoscope, for obtaining a clear image, it is necessary that the outer diameter of each of the optical fibers should be made as small as possible so that the number of optical fibers forming the image guide fiber bundle 23 is increased. Note that for reflecting light at the interface between the core 42 and the cladding layer 41, the cladding layer 41 must have significant thickness. Therefore, conventionally, an optical fiber, in which the thickness of the cladding layer 41 is 1.5 μm and the outer diameter is 8–10 μm, is used as optical fiber forming the image guide fiber bundle 23 (see FIG. 4). Thus, a ratio of the sectional area of the core 42 to the sectional area of the whole of the optical fiber (i.e., light receiving sectional area ratio) is from 39% to 49%.

On the other hand, regarding the light guide fiber bundle 21, transmittance of light to be radiated onto the observed object is important, so a relatively thick optical fiber is used. Concretely, an optical fiber, in which the thickness of the cladding layer 51 is 2 μm and the outer diameter is 25–30 μm, is used (see FIG. 5). Accordingly, a ratio of the sectional area of the core 52 to the sectional area of the whole of the optical fiber (i.e., illumination sectional area ratio) is from 70% to 75%.

Taking the matters described above into consideration, the case in which the light receiving sectional area ratio and the illumination sectional area ratio are furthest apart, is when the light receiving sectional area ratio is 39% and the illumination sectional area ratio is 75%. In this case, for equalizing the whole illumination sectional area of the light guide fiber bundle 21 to the whole light receiving sectional area of the image guide fiber bundle 23 while satisfying the optimum condition 1, a ratio of the geometrically occupied sectional area S'$_2$ of the image guide fiber bundle 23 to the geometrically occupied sectional area S'$_1$ of the light guide fiber bundle 21 should be set according to formula (7).

$$S'_2 \times 39/100 = S'_1 \times 75/100 \quad (7)$$

$$S'_2 = (75/39) \times S'_1$$

$$\approx 1.9 \times S'_1$$

Namely, for obtaining the brightest image when the image guide fiber bundle 23 composed of optical fibers, in which the light receiving sectional area ratio is 39%, and the light guide fiber bundle 21 composed of optical fibers, in which the illumination sectional area ratio is 75%, are used, the amount of optical fibers forming each of the fiber bundles 21 and 23 should be adjusted in such a manner that the geometrically occupied sectional area S'$_2$ of the image guide fiber bundle 23 is approximately 1.9 times the geometrically occupied sectional area S'$_1$ of the light guide fiber bundle 21.

On the other hand, the case in which the light receiving sectional area ratio and the illumination sectional area ratio are closest to each other, is when the light receiving sectional area ratio is 49% and the illumination sectional area ratio is 70%. In this case, for equalizing the whole illumination sectional area of the light guide fiber bundle 21 to the whole light receiving sectional area of the image guide fiber bundle 23 while satisfying the optimum condition 1, a ratio of the geometrically occupied sectional area S'$_2$ of the image guide fiber bundle 23 to the geometrically occupied sectional area S'$_1$ of the light guide fiber bundle 21 should be set according to formula (8).

$$S'_2 \times 49/100 = S'_1 \times 70/100 \quad (8)$$

$$S'_2 = (75/39) \times S'_1$$

$$\approx 1.4 \times S'_1$$

Namely, when the image guide fiber bundle 23 composed of optical fibers, in which the light receiving sectional area ratio is 49%, and the light guide fiber bundle 21 composed of optical fibers, in which the illumination sectional area ratio is 70%, are used, for obtaining the brightest image, the amount of optical fibers forming each of the fiber bundles 21 and 23 should be adjusted in such a manner that the geometrically occupied sectional area S'$_2$ of the image guide fiber bundle 23 is approximately 1.4 times the geometrically occupied sectional area S'$_1$ of the light guide fiber bundle 21.

Therefore, "When the image guide fiber bundle 23 composed of optical fibers, in which the light receiving sectional area ratio is from 39% to 49%, and the light guide fiber bundle 21 composed of optical fibers, in which the illumination sectional area ratio is from 70% to 75%, are used, if the geometrically occupied sectional area S'$_2$ of the image guide fiber bundle 23 is set to between 1.4 and 1.9 times the geometrically occupied sectional area S'$_1$ of the light guide fiber bundle 21, an image of the observed object 100 can be brightened (the optimum condition 3)."

Figure 6:
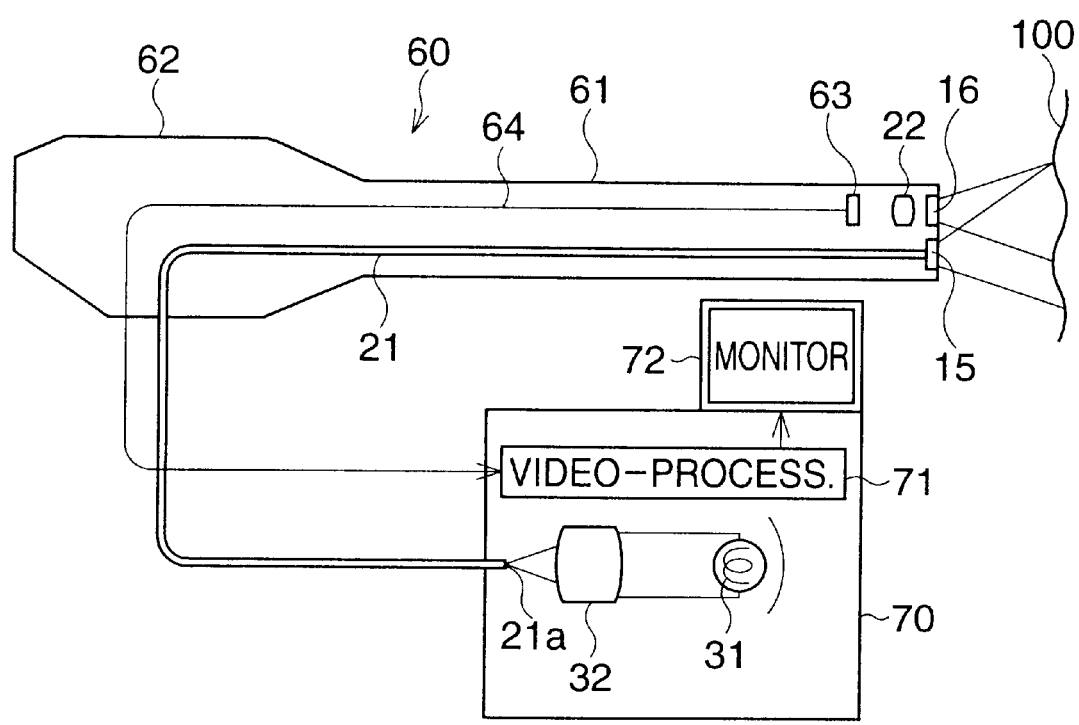
FIG. 6 is a schematic view of an endoscope system including an electronic endoscope to which a second embodiment of the present invention is applied.

FIG. 6 is a schematic view showing an endoscope system including an electronic endoscope 60 to which a second embodiment of the present invention is applied. As shown in FIG. 6, the endoscope system has the electronic endoscope 60, a light source unit 70, in which a video-processor is assembled, and a monitor 72.

The electronic endoscope 60 is provided with a probe 61, which is inserted into the inside of a body or a machine, and an operation unit 62 connected to an end portion of the probe 61. In the electronic endoscope 60, similar to the fiber-optic endoscope 10 described above, an objective lens 22, an observing window 16, a diffuser lens 15, and a light guide fiber bundle 21 are housed. Note that the electronic endoscope 60 has an imaging device (i.e., CCD area sensor) 63 and a signal cable 64, instead of the image guide fiber bundle 23 and the eyepiece 13 of the fiber-optic endoscope 10 of the first embodiment. In the imaging device 63, an image of the observed object 100 formed by the objective lens 22 is taken and converted to an image signal, which is transmitted through the signal cable 64. The output terminal of the signal cable 64 is detachably connected to the signal connector of the light source unit 70.

In the light source unit 70, similar to the light source device 30 of the first embodiment, a light source lamp 31 and a condenser lens 32 are housed. Further, in the light source unit 70, a video-processor 71 electrically connected to the signal connector is housed. The image signal, transmitted from the imaging device 63 through the signal cable 64 connected to the signal connector, is subjected to a predetermined process by the video-processor 71, so that the image signal is converted to a video signal such as an NTSC signal, and is output to the monitor 72. In the monitor 72, an image of the observed object 100 is indicated in accordance with the video signal received from the video-processor 71 of the light source unit 70.

In the electronic endoscope 60 of the endoscope system described above, a ratio of an illumination sectional area of the light guide fiber bundle 21 in the section of the probe 61 including the light receiving surface of the imaging device 63, to an effective light receiving area of the imaging device, which is an image receiving optical element, is important.

On the light receiving surface of the imaging device, a plurality of light receiving cells are arranged, and a transfer gate is provided corresponding to each of the light receiving cells, in addition to an insulating layer arranged between the light receiving cells. Therefore, the area of the whole of the light receiving surface of the imaging device 63 corresponds to the geometrically occupied sectional area of the imaging device 63, and the sum of the areas of only the light receiving cells on the light receiving surface corresponds to the effective light receiving area of the imaging device 63. A ratio of the effective light receiving area of the imaging device 63 is usually from 50% to 70%.

Thus, since the imaging device 63 of the electronic endoscope 60 can be handled in a similar way as the image guide fiber bundle 23 of the fiber-optic endoscope 10, the theory according to which the optimum conditions 1 and 2 are obtained can be applied to the electronic endoscope 60. Namely, the optimum conditions 1 and 2 are rewritten as follows:

"If the illumination sectional area of the light guide fiber bundle 21 (i.e., the sum of sectional areas of the optical fibers) and the effective light receiving area of the imaging device 63 (i.e., the sum of areas of the light receiving cells) are made equal to each other, the brightest image can be most efficiently obtained (the optimum condition 1)". "If in the accommodation space of the probe 11, a ratio of the illumination sectional area $S_1$ of the light guide fiber bundle 21 to the effective light receiving area $S_2$ of the imaging device 63 is set as shown in formula (9), $$39:61 < S_1 : S_2 < 61:39 \quad (9)$$

an image of the observed object 100 can be obtained with sufficient brightness which is more than or equal to 95% of the maximum brightness (the optimum condition 2')".

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2000-209898 (filed on Jul. 11, 2000) which is expressly incorporated herein, by reference, in its entirety.

What is claimed is:

1. A probe of an endoscope, comprising
  a distal end in which an objective lens is disposed;
  a light guide fiber bundle that supplies illumination light to the distal end to form an illumination sectional area from which said illumination light is radiated, said light guide fiber bundle being formed by bundling second optical fibers, and said illumination sectional area being the sum of sectional areas of cores of said second optical fibers; and
  an image receiving optical element that transmits an image of the observed image obtained by said objective lens, said image receiving optical element comprising an image guide fiber bundle formed by bundling first optical fibers and said image receiving optical element further comprising a light receiving area, said light receiving area corresponding to the sum of sectional areas of cores of said first optical fibers;
  a ratio of said illumination sectional area of said light guide fiber bundle to said light receiving area of said image receiving optical element is greater than or equal to 39/61 and less than 50/50.

2. A problem according to claim 1, wherein a geometrically occupied sectional area of said image guide fiber bundle is between 1.4 and 1.9 times a geometrically occupied sectional area of said light guide fiber bundle.

3. A probe of an endoscope, comprising:
  a light guide fiber bundle that supplies illumination light to a distal end of said probe, said light guide fiber bundle being formed by bundling second optical fibers so that said illumination light is radiated onto an observed object so that the illumination light is reflected by the observed object; wherein an illumination sectional area of said light guide fiber bundle is the sum of sectional areas of cores of said second optical fibers; and
  an image receiving optical element that receives the reflected light, said image receiving optical element comprising an image guide fiber bundle formed by bundling first optical fibers and a light receiving area, said light receiving area corresponding to the sum of sectional areas of cores of said first optical fibers;
  a ratio of said illumination sectional area to said light receiving area of said image receiving optical element is greater than or equal to 39/6 1 and less than 50/50.

4. A probe of an endoscope, comprising
  a distal end in which an objective lens is disposed;
  a light guide fiber bundle that supplies illumination light to the distal end to form an illumination sectional area from which said illumination light is radiated, said light guide fiber bundle being formed by bundling second optical fibers, and said illumination sectional area being the sum of sectional areas of cores of said second optical fibers; and
  an image receiving optical element that transmits an image of the observed image obtained by said objective lens, said image receiving optical element comprising an image guide fiber bundle formed by bundling first optical fibers and said image receiving optical element further comprising a light receiving area, said light receiving area corresponding to the sum of sectional areas of cores of said first optical fibers;
  a ratio of said illumination sectional area of said light guide fiber bundle to said light receiving area of said image receiving optical element is greater than 50/50 and less than 60/40.

5. A problem according to claim 4, wherein a geometrically occupied sectional area of said image guide fiber bundle is between 1.4 and 1.9 times a geometrically occupied sectional area of said light guide fiber bundle.

6. A probe of an endoscope, comprising:
  a light guide fiber bundle that supplies illumination light to a distal end of said probe, said light guide fiber bundle being formed by bundling second optical fibers so that said illumination light is radiated onto an observed object so that the illumination light is reflected by the observed object; wherein an illumination sectional area of said light guide fiber bundle is the sum of sectional areas of cores of said second optical fibers; and
  an image receiving optical element that receives the reflected light, said image receiving optical element comprising an image guide fiber bundle formed by bundling first optical fibers and a light receiving area, said light receiving area corresponding to the sum of sectional areas of cores of said first optical fibers;
  a ratio of said illumination sectional area to said light receiving area of said image receiving optical element is greater than 50/50 and less than 60/40.

* * * * *